United States Patent [19]
Buchbinder et al.

[11] Patent Number: 5,376,074
[45] Date of Patent: * Dec. 27, 1994

[54] OUTER EXCHANGE CATHETER SYSTEM

[75] Inventors: Maurice Buchbinder; Ronald J. Solar, both of San Diego, Calif.

[73] Assignee: Medtronic, Inc., Minneapolis, Minn.

[*] Notice: The portion of the term of this patent subsequent to Jul. 31, 2007 has been disclaimed.

[21] Appl. No.: 63,348

[22] Filed: May 18, 1993

Related U.S. Application Data

[63] Continuation of Ser. No. 531,071, May 31, 1990, abandoned, which is a continuation of Ser. No. 235,829, Aug. 18, 1988, Pat. No. 4,944,740, which is a continuation of Ser. No. 909,446, Sep. 19, 1986, abandoned, which is a continuation-in-part of Ser. No. 651,806, Sep. 18, 1984, abandoned.

[51] Int. Cl.⁵ .............................................. A61M 25/00
[52] U.S. Cl. ............................................ 604/96; 606/194
[58] Field of Search ............................ 604/53, 96–104; 606/159, 194

[56] References Cited

U.S. PATENT DOCUMENTS

| | | | |
|---|---|---|---|
| 4,195,637 | 4/1980 | Gr/ntzig et al. | 604/97 |
| 4,215,703 | 8/1980 | Willson | 128/772 |
| 4,299,926 | 11/1981 | Banka | 606/194 |
| 4,323,071 | 4/1982 | Simpson et al. | 604/98 |
| 4,370,982 | 2/1983 | Reilly | 604/98 |
| 4,445,509 | 5/1984 | Auth | 606/159 |
| 4,456,000 | 6/1984 | Schjeldahl | 606/194 |
| 4,456,017 | 6/1984 | Miles | 128/772 |
| 4,545,390 | 10/1985 | Leary | 604/96 |
| 4,582,181 | 4/1986 | Samson | 604/95 |
| 4,616,652 | 10/1986 | Simpson | 606/194 |
| 4,944,740 | 7/1990 | Buchbinder et al. | 606/194 |
| 4,976,689 | 12/1990 | Buchbinder et al. | 606/194 |
| 5,040,548 | 8/1991 | Yock | 606/194 |

*Primary Examiner*—Ralph A. Lewis
*Attorney, Agent, or Firm*—Dianne M. F. Plunkett; Harold R. Patton

[57] ABSTRACT

This invention relates to corporeal catheters. More particularly, this invention relates to an outer exchange catheter system comprising an outer catheter sheath and at least one steerable inner catheter having a control means, said outer catheter sheath extending less than the full length of each said inner catheter and being slidable thereover.

4 Claims, 2 Drawing Sheets

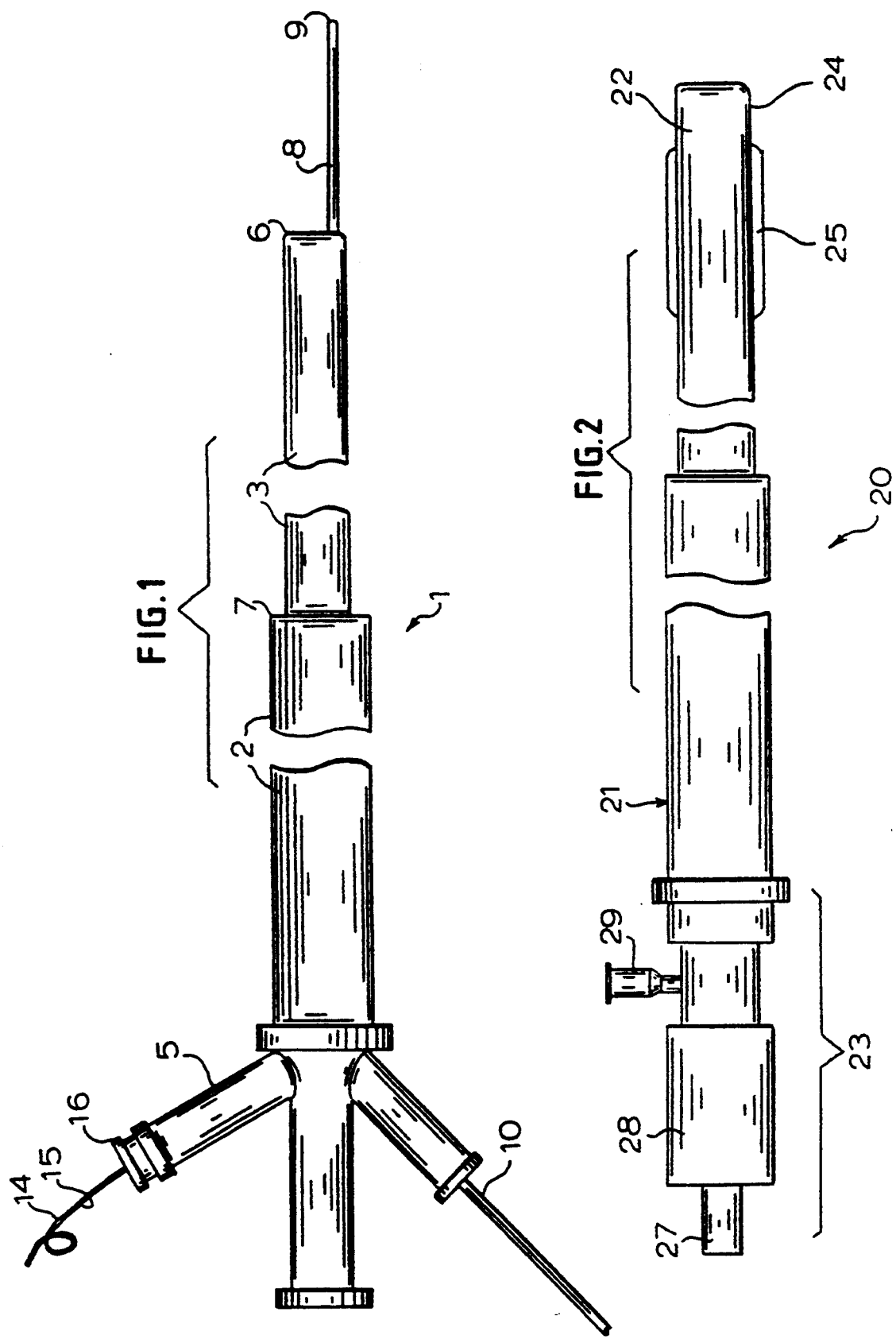

OUTER EXCHANGE CATHETER SYSTEM

This is a continuation of copending application(s) Ser. No. 07/531,071 filed on May 31, 1990 and now abandoned, which is a continuation of U.S. Ser. No. 07/235,829 filed on Aug. 18, 1988 U.S. Pat. No. 4,944,740; which is a continuation of U.S. Ser. No. 06/909,446, filed Sep. 19, 1986, abandoned; which is a continuation in part of U.S. Ser. No. 06/651,806, filed Sep. 18, 1984 abandoned.

FIELD OF THE INVENTION

This invention relates to corporeal catheters. More particularly, this invention relates to a catheter system useful in cardiovascular applications wherein the catheter has a movable outer sheath to permit standard exchange techniques.

BACKGROUND OF THE INVENTION

Catheters comprise tube-like members that are inserted into the body for various medical reasons, some diagnostic and others therapeutic. While in many instances the steerability or directionality of such catheters is of concern, steerability is particularly important with regard to certain urological or cardiovascular applications.

There have been various attempts to develop steerable catheters. For example, U.S. Pat. No. 1,060,665 describes an early attempt to provide a catheter capable of some direction. However, the device disclosed in this patent, as well as catheters and catheter guides disclosed in later patents, such as U.S. Pat. Nos. 2,574,840 and 2,688,329, tend to be characterized by only limited directionality.

In addition, some supposedly steerable catheters are too large and rigid to be of practical use in cardiovascular techniques. See, for example, U.S. Pat. Nos. 3,470,876 and 3,605,725, where wires equidistantly positioned along the length of a catheter are connected to a steering means which pulls on the wires to cause the distal end of the catheter to go in a desired direction. Moreover, U.S. Pat. Nos. 3,521,620, 3,547,103, 3,625,200, and 4,020,829 describe coil spring guide wires that have a certain degree of directionality but are too rigid for safe usage in certain delicate cardiovascular procedures.

According to U.S. Pat. No. 4,033,331, a coronary catheter has a main lumen and a shaping wire lumen. When the wire is withdrawn through the shaping wire lumen, the catheter assumes certain predetermined configurations. While this so-called steerable catheter is useful in some cardiovascular applications, such as positioning the initial guiding catheter guide through which other devices are guided, its limited directionality and limited tip control preclude extensive use.

A medical procedure known as percutaneous transluminal coronary angioplasty (PTCA) was developed in approximately 1976–1977 by Dr. Andreas Grüntzig. According to this procedure, blockage in a coronary artery can be reduced by positioning a balloon dilatation catheter across the blockage and inflating the balloon, which causes the blockage to decrease. Such positioning requires that the balloon dilatation catheter be "steered" into place, that is, across the stenotic lesion causing the blockage, by manipulation at the proximal end of the catheter.

The procedure is actually somewhat complex, consisting of introducing a catheter system via the femoral or brachial artery under local anesthesia. A pre-shaped guiding catheter is positioned into the orifice of the coronary artery, and through this guiding catheter a second dilatation catheter is advanced into the branches of the coronary artery. The dilatation catheter has an elliptically shaped balloon portion near the tip which can be inflated and deflated. After traversal of the stenotic lesion of the coronary artery, the balloon portion is inflated with fluid, which dilates the lumen of the vessel.

The PTCA procedure and equipment have become increasingly refined over the past six years. The first marketable PTCA apparatus consisted of a small catheter with a single balloon port and no central lumen, that is, a so-called "fixed wire" system, which terminated in lateral openings at the distal end thereof. This system, which is the subject of U.S. Pat. No. 4,195,637, was designed by Dr. Grüntzig and was marketed in the United States by USCI. The fixed wire catheter system disclosed in U.S. Pat. No. 4,195,637 comprises a balloon dilatation catheter and a low friction guide catheter consisting of one tubular member fitted into a more rigid, shrunk-on tubular member that is not co-extensive. The distal end of the balloon dilatation catheter has a flexible tip advantageously fabricated from a spring steel wire.

In 1980–1981 Dr. John Simpson, working at Stanford University, began to modify the fixed wire system and eventually developed a catheter with a free central lumen for movable guide wires. This catheter system is the subject of U.S. Pat. No. 4,323,071, which is assigned to Advanced Cardiovascular Systems, Inc. (ACS), formerly known as Advanced Catheter Systems, Inc. By use of such a movable wire system, one could more readily select the desired coronary artery and reach smaller branches since the movable guidewires are inherently smaller and more flexible than the fixed wire system. Movable guidewires are particularly useful in a technique known as catheter exchange, whereby one catheter positioned concentrically around a guidewire is replaced by, i.e., exchanged for, another such catheter, the guidewire maintaining the desired position. Subsequent to the development of the catheter with movable guidewires, known as the Simpson-Robert system and marketed by ACS, USCI has abandoned the fixed wire system and has marketed a similar device, calling it the steerable catheter, DILACA ®.

Samson, U.S. Pat. No. 4,516,972 issued May 14, 1985, to ACS. This patent is directed to a guide catheter having a helically wound ribbon of flexible material imbedded in the wall of the catheter to provide torsional rigidity.

There is a further catheter system in use known as the Hartzler low profile catheter system. According to this catheter system a balloon dilatation catheter has a concentrically contained guidewire extending the length of said catheter. Moreover, the distal end of the guidewire extends a short distance beyond the distal end of the balloon dilatation catheter and is affixed to the distal end of the balloon dilatation catheter.

The catheter system with movable guidewires and the low profile catheter system each represent an advance but still have disadvantages such as limited steerability, which is at present dependent upon the torquability, or torque control, of the movable wire. Steerability is highly significant in a cardiovascular procedure such as PTCA, or angioplasty, because less steerability results in greater time spent in the body and more possible patient trauma. Multiple insertions of guidewires and catheters can lead to thrombosis in that coagulation may commence along a guidewire surface and be forced into the heart when a catheter is slid over the guidewire. Furthermore, there are some blockages which simply cannot be reached with presently known equipment.

Co-pending U.S. patent application Ser. No. 651,806, filed Sep. 18, 1984 (abandoned), U.S. patent application Ser. No. 774,345, filed Sep. 10, 1985 (abandoned), and U.S. Pat. No. 4,723,936, filed Jul. 22, 1986, all of which are incorporated herein by reference, are directed to improved steerable catheter means useful in, for example, cardiovascular applications. The catheter means disclosed therein are characterized by a relatively low profile and enhanced directionality due to combined rotation of the catheter means and active deflection of the catheter tip.

As mentioned above, PTCA technology appears to be directed toward fixed wire dilatation catheters, especially low profile catheters. To achieve such low profiles, it has been necessary to abandon the through lumen of the movable guidewire catheter, a design change which has precluded standard exchange techniques wherein dilatation balloons are changed over a guidewire. In addition, a guidewire cannot be maintained in position across and past a stenosis once dilatation is complete because as soon as a fixed wire catheter is withdrawn, the position across and beyond the stenosis is lost.

OBJECTS OF THE INVENTION

It is an object of the invention to provide an improved catheter system.

It is also an object of the invention to provide a steerable catheter system useful in cardiovascular applications.

It is a further object of the invention to provide a catheter system having an outer sheath useful for outer exchange.

These and other objects of the invention will become more apparent in the discussion below.

BRIEF DESCRIPTION OF THE DRAWINGS

FIGS. 1 and 2 each represent a planar view of an embodiment of the invention;

DETAILED DESCRIPTION OF THE INVENTION

Figure 3:
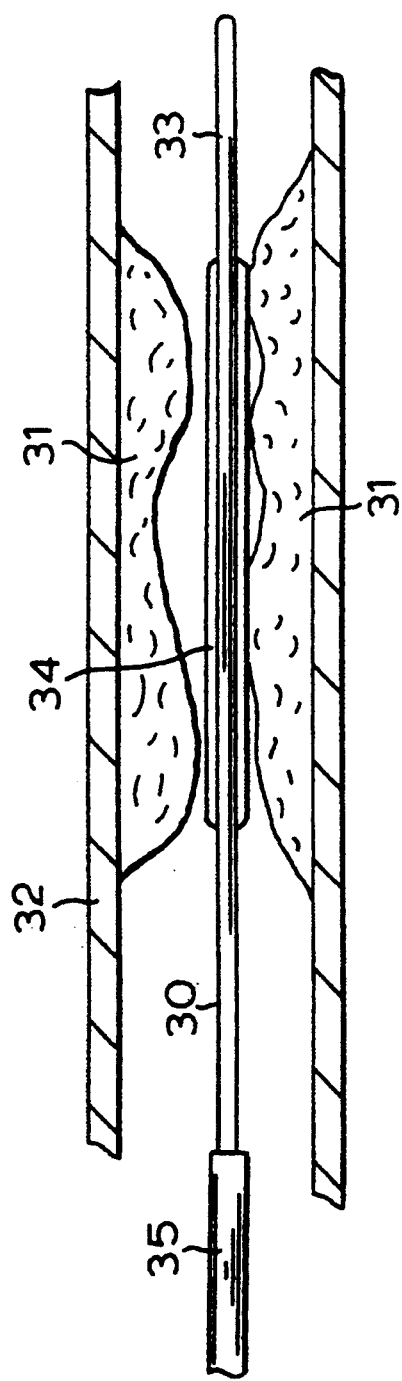
FIG. 3 represents a partially sectional view where an embodiment of the invention has been positioned across a stenosis in an artery.

Applicants have surprisingly developed a flexible and steerable catheter means, or delivery means, which is more useful than those known. According to the invention, a catheter means comprises a catheter, such as a fixed wire, steerable catheter, having a sleeve, an outer shell or sheath, which facilitates exchange capabilities. The sleeve extends from the proximal end of the catheter to a point approximately one-third from the distal end of the catheter, i.e., it covers about two-thirds of the catheter. In this arrangement, the sheath can slide easily and freely over the catheter and, if desired, be advanced over the distal end of the catheter.

This invention is especially intended for use with a dilatation catheter or dilatation catheter system wherein the distal end comprises dilatation balloon means to be placed across a stenosis. Once a stenosis has been crossed with the dilatation balloon, the sheath can be advanced over the distal tip of the dilatation catheter beyond the stenosis. More specifically, once a dilatation balloon of lowest available profile has crossed the stenosis and dilatation has taken place, the sheath being in retracted position, the sheath is then advanced or slid over the tip of the dilatation catheter beyond the area of stenosis. The catheter can then be withdrawn, leaving the outer sheath across and beyond the stenosis without the catheter inside it.

With such a system as described above, distal pressure beyond the area of stenosis could theoretically be measured, for example, with a pressure sensing membrane at the distal end of an optical fiber. Also, with the dilatation catheter removed, distal dye could be injected to inspect arterial flow beyond the site dilated, or other agents such as localized thrombolytic agents, vasodilators, or the like, could be injected. Further, a larger dilatation balloon could be introduced. The introduction of a larger balloon, or the exchange from a smaller to a larger balloon, would be much simpler than over a wire since the sheath is already in place across and beyond the area of stenosis, and the only maneuver the operator has to perform is to advance the dilatation balloon of desired size inside the sheath.

The sheath could also act as a coronary shunt in the event of abrupt closure of a vessel. In such a case, the dilatation catheter will be pulled out, the sheath alone being maintained beyond the area of complete occlusion. This would provide flow distally, similar to the ACS reperfusion catheter concept.

It should be noted that the so-called outer exchange sleeve or sheath does not alter the profile of the catheter since it does not extend all the way to the distal tip of the dilatation catheter or over the dilatation balloon. In retracted position it is approximately one-third of the way from the distal tip, and it is advanced over the dilatation balloon only when needed after dilatation has taken place.

Another aspect of this invention is that the presence of the outer sheath can improve the efficacy of a catheter such as a dilatation catheter. It is believed that the outer sheath in some manner improves the effectiveness and/or manuverability of certain dilatation catheters due to any stiffness or support provided, that is, additional support for the catheters enable them to negotiate tortuous paths and cross tight stenoses.

With respect to exchanging catheters, the exchange would be accomplished according to the invention in a less traumatic manner than current technology allows. Presently, catheter exchange takes place over a guidewire, a very time-consuming process (about 15 minutes), which requires additional fluoroscopic exposure. The guidewire is first exchanged for a longer "exchange wire," which exchange carries the risk of thromboembolism. Next, the balloon dilatation cather is withdrawn, and it rubs against the lining of the artery (the intima). This could result in intimal damage (denudation of the endothelial layer), which may subsequently cause thrombus formation (clot). After the first catheter is removed, a second dilatation catheter is passed over the exchange wire, and once again this may result in intimal damage. Thus, each catheter exchange results in two additional passes of the catheter against the arterial lining, and the more the intima is "roughed", the greater is the chance of thrombolic complications. With the outer sheath design herein, catheter exchanges take place within the sheath, i.e., the "exchanged" catheters do not touch the arterial wall during passage. Moreover, a set of calibrated marks may be on the catheter and sheath so that insertion of subsequent catheters can be done without fluoroscopy (less radiation exposure and dye injection).

As mentioned above, the invention herein is directed to an outer exchange catheter system whereby a catheter such as a dilatation catheter has an outer sheath. More particularly, such catheter systems comprise:

an outer flexible catheter sheath having distal and proximal ends, and at least one inner flexible catheter having distal and proximal ends and one or more lumens, each inner catheter extending through the outer catheter sheath and being slidable therein, and the distal end of each inner catheter protruding substantially beyond the distal end of the outer catheter sheath.

In another embodiment of the invention, such catheter systems comprise:

an outer flexible catheter sheath having distal and proximal ends, at least one inner flexible catheter having distal and proximal ends and one or more lumens, each inner catheter extending through the outer catheter sheath and being slidable therein, and the distal end of each inner catheter protruding substantially beyond the distal end of the outer catheter shell, and at least one inner catheter having one of said lumens closed at its distal end, a deflection or steering wire having distal and proximal ends and extending the length of said inner catheter through the lumen having the closed end, the distal end of the deflection wire being embedded in said closed end, and control means attached to the proximal end of at least one inner catheter.

The proximal end of the deflection wire extends through such control means, and the control means has an engaging means which fixedly engages said deflection wire to cause the deflection wire to longitudinally displace either toward or away from the distal end thereof, said displacement causing, the distal end of the inner catheter to bend out of or toward the plane of the longitudinal axis of the inner catheter. The control means can be rotated to cause the distal end of an inner catheter to rotate.

The open lumens within an inner catheter may carry various objects and/or function as other than mere conduits for such objects. For example, an open lumen may contain a fixed or movable guidewire, a retractable pressure sensing fiber, or an inflatable dilatation balloon. Also, radiopaque fluids or active substances may be transmitted through a lumen, or a lumen itself may be used as a pressure sensing means.

An inner flexible catheter can be virtually any of the known dilatation catheters, including, but not limited to, the catheters described above. This invention is especially directed to the catheters and catheter systems described in the aforementioned U.S. patent applications Ser. Nos. 651,806 (abandoned) and, 774,345 (abandoned), and U.S. Pat. No. 4,723,936, specifically incorporated herein by reference with regard to the dimensions, materials, and construction of said catheters.

In additional embodiments of the invention, an inner catheter may comprise:

(A) a flexible catheter having distal and proximal ends and one or more lumens extending therethrough, at least one of said lumens being closed at its distal end, a deflection wire having distal and proximal ends and extending the length of a lumen having a closed end, the distal end of the deflection wire being embedded in said closed end, and control means attached to the proximal end of the catheter, the proximal end of the deflection wire extending through the control means and the control means having an engaging means which fixedly engages said deflection wire to cause the deflection wire to longitudinally displace either toward or away from the distal end thereof, said displacement causing the distal end of the inner catheter to bend out of or toward the plane of the longitudinal axis of the catheter, and the control means being capable of being rotated such that the distal end of the catheter rotates;

(B) a flexible catheter comprising a spring coil body defining a lumen, each of said catheter and said spring coil body having proximal and distal ends, the distal end of said spring coil body being closed, and said spring coil body having a flexible covering thereon, dilatation balloon means positioned concentrically around the distal end of said spring coil body, a deflection wire having proximal and distal ends being substantially co-extensive with said spring coil body, the distal end of said deflection wire being attached to the distal end of said spring coil body, and control means attached to the proximal end of said catheter, the proximal end of said deflection wire extending through the control means, the control means having engaging means which fixedly engages the proximal end of said deflection wire to cause said deflection wire to be displaced distally or proximally, said displacement causing the distal end of said catheter to bend out of or toward the plane of its longitudinal axis, and the control means having rotation means capable of causing said catheter to rotate about its longitudinal axis;

(C) a flexible catheter comprising a spring coil body defining a lumen, each of said catheter and said spring coil body having proximal and distal ends, the distal end of said spring coil body being closed, and said spring coil body having a flexible covering thereon, dilatation balloon means positioned concentrically around the distal end of said spring coil body, and control means attached to the proximal end of said catheter, said control means having rotating means capable of causing said catheter to rotate about its longitudinal axis;

(D) a flexible catheter comprising a spring coil body defining a lumen, said spring coil body having proximal and distal ends, a flexible tip having proximal and distal ends, the proximal end of said flexible tip being positioned a short distance from the distal end of said spring coil body to form a discontinuity, and a flexible covering, said flexible covering extending from the proximal end of said spring coil body along the length of said spring coil body across said discontinuity to the proximal end of said proximal tip, a dilatation balloon means positioned around said discontinuity, a deflection wire having proximal and distal ends, said deflection wire extending substantially co-extensively with said spring coil body, the distal end of said deflection wire being attached to the proximal end of said flexible tip, and control means having engaging means which fixedly engages the proximal end of said deflection wire to cause said deflection wire to be displaced distally or proximally, said displacement causing the distal end of said catheter to bend out of or toward the plane of its longitudinal axis, and the control means being capable of causing said catheter to rotate about its longitudinal axis;

(E) a flexible catheter comprising a spring coil body defining a lumen, each of said catheter and said spring coil body having proximal and distal ends, the distal end of said spring coil body being open, a deflection wire having proximal and distal ends and being substantially co-extensive with said spring coil body, the distal end of said deflection wire being attached to the distal end of said spring coil body, and control means attached to the proximal end of said catheter, the proximal end of said deflection wire extending through the control means, the control means having engaging means which fixedly engages the proximal end of said deflection wire to cause said deflection wire to be displaced distally or proximally, said displacement causing the distal end of said catheter to bend out of or toward the plane of its longitudinal axis, and the control means being capable of causing said catheter to rotate about its longitudinal axis; or (F) a flexible catheter comprising a spring coil body defining a lumen, each of said catheter and said spring coil body having proximal and distal ends, the distal end of said spring coil body being open, and said spring coil body having a flexible covering thereon, and control means attached to the proximal end of said catheter, said control means being capable of causing said catheter to rotate about its longitudinal axis.

The invention can perhaps be better understood by making reference to the drawings. In FIG. 1, catheter system 1 is essentially comprised of outer catheter sheath or shell 2, inner catheter 3, deflection wire 4, and control means 5. Outer sheath 2 encloses a substantial portion of inner catheter 3, from about 40% to 90%, preferably from about 55% to 75%, of inner catheter 3. Inner catheter 3 is freely rotatable and slidable within outer sheath 2. Distal end 6 of inner catheter 3 projects out of the distal end 7 of outer sheath 2.

A movably controlled, or movable, guidewire 8 extends the length of catheter system 1, the distal end 9 of movable guidewire 8 projecting out of inner catheter 3 and the proximal end 10 of movable guidewire 8 extending through control means 5. Inner catheter 3 may have, for example, two lumens, one open lumen through which movable guidewire 8 is introduced, and a lumen in which the distal end is closed. The distal end of deflection wire 4 would be embedded from about 0.1 to 7 centimeters, preferably from about 1 to 5 centimeters, into said closed distal end.

The proximal end of steering wire 4 extends through control means 5 and is fixedly held by engaging means 16. Turning engaging means 16 causes wire 4 to shorten or lengthen relative to inner catheter 3, which in turn causes distal end 6 of inner catheter 3 to bend away from longitudinal axis of outer sheath 2.

The embodiment of the invention shown in FIG. 2 comprises a catheter system 20 essentially comprised of outer sheath 21, inner catheter 22, and control means 23. Inner catheter 22 is fully rotatable and/or slidable within outer sheath 21. Distal end 24 of inner catheter 22 comprises dilatation balloon means 25, shown in deflated position.

The proximal portion (not shown) of inner catheter 22 is connected to the distal portion of control means 23. Also, catheter 22 has a deflection wire therein (not shown) which is connected to engaging means (not shown) within control means 23. Turning control knob 27 causes the distal end 24 of inner catheter 23 to deflect, and rotation of surface 28 causes distal end 24 to rotate.

Inflation port 29 is in fluid communication with dilatation balloon means 25. In an alternative arrangement, inflation port 29 may be arranged concentrically around the longitudinal axis of control knob 27.

Figure 4:
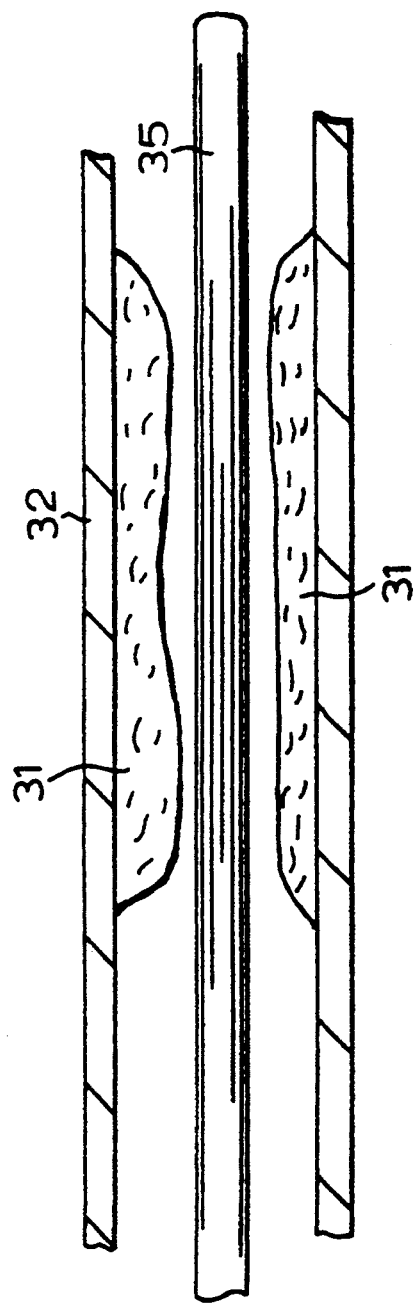
FIG. 4 represents a partially sectional view of FIG. 3 after dilatation of the stenosis and advancement of the outer sheath.

FIGS. 3 and 4 show an embodiment of the invention across a stenosis. In FIG. 3, a balloon dilatation catheter 30 has been advanced across a stenosis 31. The distal end 33 of the catheter is past stenosis 31, and the dilatation balloon 34 is positioned across the stenosis itself. Outer sheath 35 is withdrawn.

After dilatation, the outer sheath 35 is advanced across and past the stenosis 31, as in FIG. 4. Outer sheath 35 is left in position while dilatation catheter 30 is withdrawn.

As discussed above, the outer sheath is slidable over each inner catheter. Such slidability is due either to the particular materials of which the outer sheath and each inner sheath are respectively comprised and/or any coating or treatment that may be applied to one or more surfaces. For example, the outer catheter and/or each inner catheter may be comprised of a suitable lubricous polymeric material, such as those selected from the group consisting of polyethylene, polyvinyl chloride, polypropylene, polytetrafluoroethylene, and copolymers thereof. In addition, the outer surface of an inner catheter and/or the inner surface of the outer sheath may have a coating thereon which promotes or facilitates slidability. Suitable such coatings, such as effective amounts of a material selected from the group consisting of hydrogels, silicones, and fluoropolymers such as polytetrafluoroethylene, are well known to those skilled in the art.

It is disclosed herein that an inner catheter may comprise one or more lumens. Advantageously such catheters comprise from one to four lumens, preferably from one to three lumens, and more preferably one or two lumens.

Furthermore, it is within the scope of the invention that the outer sheath may function as a shunt across a stenosis or blockage within an artery or other corporeal passageway. To facilitate such an arrangement, the outer sheath would comprise small perforations or openings of suitable size and number to permit (i) entry into the outer sheath at a point proximal to the stenosis or blockage and (ii) exit from the sheath at a point distal to the stenosis or blockage. Said perforations, which would have to be of a small enough size and/or number that the structural integrity of the sheath would not be compromised, could be circular, oval, slotted, or the like. For example, an arrangement of perforations could comprise from 3 to 10 equidistantly positioned circular holes of from 0.25 to 2.5 mm in diameter, around the circumference of the outer sheath.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A method for dilating a stenosis in a passageway in a body, which comprises:
   a. introducing an outer sheath having proximal and distal ends and a lumen into a body passageway;
   b. advancing a first catheter having a dilatation balloon means adjacent to a distal end thereof, into and through the outer sheath to cause the dilatation balloon means to be positioned across a stenosis in the body passageway;
   c. inflating the first dilatation balloon means to cause the stenosis to dilate:
   d. deflating the first dilatation balloon means;
   e. slidably advancing the outer sheath distally along the first dilatation catheter to position the outer sheath distally of the stenosis; and
   f. withdrawing the first dilatation catheter in the proximal direction within the outer sheath to remove the first dilatation catheter from the body.

2. A method of dilating a stenosis in a passageway in a body according to claim 1 further comprising:
   a. advancing a second dilatation catheter having proximal and distal ends and a second dilatation means distally within the outer sheath to cause the second dilatation means to be positioned across the stenosis;
   b. moving the distal end of the outer sheath proximal of the stenosis;
   c. dilating the stenosis; and
   d. withdrawing the second dilatation catheter from the body passageway.

3. A method of dilating a stenosis in a passageway in a body according to claim 2 wherein the second dilatation means of the second dilatation catheter comprises a balloon means.

4. A method for dilating a stenosis in a passageway in a body, which comprises:
   a. introducing an outer sheath having proximal and distal ends and a lumen into a body passageway;
   b. advancing a first catheter having a dilatation balloon means adjacent to a distal end thereof, into and through the outer sheath to cause the dilatation balloon means to be positioned across a stenosis in the body passageway;
   c. inflating the first dilatation balloon means to cause the stenosis to dilate;
   d. deflating the first dilatation balloon means;
   e. slidably advancing the outer sheath distally along the first dilatation catheter to position the outer sheath distally of the stenosis;
   f. withdrawing the first dilatation catheter in the proximal direction within the outer sheath to remove the first dilatation catheter from the body;
   g. advancing a second dilatation catheter having proximal and distal ends and a second balloon dilatation means distally within the outer sheath to cause the second balloon dilatation means to be positioned across the stenosis:
   h. moving the distal end of the outer sheath proximal of the stenosis:
   i. inflating the second balloon dilatation means;
   j. deflating the second balloon dilatation means; and
   k. withdrawing the second dilatation catheter from the body passageway.

* * * * *